United States Patent
Li et al.

(10) Patent No.: US 9,333,063 B2
(45) Date of Patent: May 10, 2016

(54) ANTIMICROBIAL MEDICAL DEVICES

(75) Inventors: Jianmin Li, Lexington, MA (US); Min-Shyan Sheu, Chelmsford, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1731 days.

(21) Appl. No.: 12/437,099

(22) Filed: May 7, 2009

(65) Prior Publication Data

US 2009/0281635 A1 Nov. 12, 2009

Related U.S. Application Data

(60) Provisional application No. 61/051,695, filed on May 9, 2008.

(51) Int. Cl.

| | | |
|---|---|---|
| A61F 2/82 | (2013.01) | |
| A61F 2/90 | (2013.01) | |
| A61F 2/00 | (2006.01) | |
| A61L 31/02 | (2006.01) | |
| A61L 31/08 | (2006.01) | |
| A61L 31/18 | (2006.01) | |
| A61M 25/00 | (2006.01) | |
| A61M 27/00 | (2006.01) | |
| A61F 2/04 | (2013.01) | |
| A61F 2/94 | (2013.01) | |
| B05D 1/18 | (2006.01) | |
| B05D 1/26 | (2006.01) | |

(52) U.S. Cl.
CPC ............ *A61F 2/0045* (2013.01); *A61L 31/022* (2013.01); *A61L 31/088* (2013.01); *A61L 31/18* (2013.01); *A61M 25/0017* (2013.01); *A61M 27/008* (2013.01); *A61F 2/0063* (2013.01); *A61F 2/04* (2013.01); *A61F 2/94* (2013.01); *A61L 2400/12* (2013.01); *B05D 1/18* (2013.01); *B05D 1/26* (2013.01); *B05D 2601/28* (2013.01)

(58) Field of Classification Search
USPC ............ 623/1.42–1.46, 23.66, 23.7; 424/423; 427/2.25
See application file for complete search history.

(56) References Cited

U.S. PATENT DOCUMENTS

| | | | |
|---|---|---|---|
| 4,902,503 A | 2/1990 | Umemura et al. | |
| 5,049,140 A | 9/1991 | Brenner et al. | |
| 5,505,695 A | 4/1996 | Eplett, Jr. | |
| 5,681,274 A * | 10/1997 | Perkins et al. | .................... 604/8 |
| 5,928,174 A | 7/1999 | Gibbins | |
| 6,277,108 B1 | 8/2001 | McBroom et al. | |
| 6,355,858 B1 | 3/2002 | Gibbins | |
| 6,605,751 B1 | 8/2003 | Gibbins et al. | |
| 6,897,349 B2 | 5/2005 | Gibbins et al. | |

(Continued)

FOREIGN PATENT DOCUMENTS

WO          WO0074633 A2    12/2000

OTHER PUBLICATIONS

Fred E. Govier et al., "Pubocaginal slings: a review of the technical variables," Curr. Opin Urol. 2001,11, pp. 405-410.
John Klutke et al., "The promise of tension-free vaginal tape for female SUI," Contemporary Urol., Oct. 2000, pp. 59-60, 65-66, 69-70, 73.
"NanoDynamics is Commercializing Nanosilver for Electronics and Healthcare," Apr. 4, 1996, 2 pp. Downloaded from www.ndmaterials.com on Sep. 13, 2007.

(Continued)

*Primary Examiner* — Yashita Sharma
(74) *Attorney, Agent, or Firm* — Kacvinsky Daisak Bluni PLLC

(57) ABSTRACT

According to an aspect of the present invention, medical devices are provided whose surfaces are partially covered with a coating that further comprises silver nanoparticles. Other aspects of the invention pertain to methods of making and using such medical devices.

15 Claims, 2 Drawing Sheets

(56) References Cited

U.S. PATENT DOCUMENTS

| | | |
|---|---|---|
| 2004/0147618 A1 | 7/2004 | Lee et al. |
| 2005/0008676 A1* | 1/2005 | Qiu et al. .................. 424/429 |
| 2005/0025800 A1 | 2/2005 | Tan |
| 2005/0078158 A1 | 4/2005 | Magdassi et al. |
| 2006/0065075 A1* | 3/2006 | Chang et al. .................. 75/371 |
| 2006/0189113 A1 | 8/2006 | Vanheusden et al. |
| 2006/0210700 A1 | 9/2006 | Lachner |
| 2006/0254387 A1 | 11/2006 | Lee et al. |
| 2007/0003603 A1 | 1/2007 | Karandikar et al. |
| 2007/0018140 A1 | 1/2007 | Lee et al. |
| 2007/0034052 A1 | 2/2007 | Vanheusden et al. |

OTHER PUBLICATIONS

F. Furno et al., "Silver nanoparticles and polymeric medical devices: a new approach to prevention of infection?" Journal of Antimicrobial Chemotherapy, 2004, 54 pp. 1019-1024.

Bruce L. Gibbins, "SilvaGard™ Technology Summary," 2005, 8 pp.

Bruce L. Gibbins, "Novel Antimicrobial Treatment," Jul. 2005, 5 pp.

Powers, "Antimicrobial silver nanoparticles eliminate biofilm formation on medical devices," NanoBiotech News, Aug. 10, 2005, 2pp.

Products | Materials | Metals | Silver, 2007, Nanodynamics®, 2 pp., downloaded from www.ndmaterials.com on Dec. 21, 2007.

* cited by examiner

ANTIMICROBIAL MEDICAL DEVICES

STATEMENT OF RELATED APPLICATIONS

This application claims the benefit of U.S. Provisional Patent Application Ser. No. 61/051,695, filed May 9, 2008, entitled "Antimicrobial Medical Devices", which is incorporated in its entirety by reference herein.

FIELD OF THE INVENTION

The present invention relates generally to medical devices, and more particularly to medical devices having antimicrobial properties.

BACKGROUND OF THE INVENTION

Numerous medical devices are known, which are required to sustain their aseptic properties over a period of time. One solution to this problem is to produce a medical device containing a dispersed antimicrobial agent, which releases the antimicrobial agent over an extended period.

It is known that certain heavy metals such as gold, silver, copper and zinc as well as compounds thereof exert an antimicrobial effect on a wide spectrum of microorganisms, including various bacteria and fungi, at very low metal ion concentrations. This effect is called an oligodynamic effect. Moreover, medical devices have been produced which take advantage of this effect. See, e.g., U.S. Pat. No. 4,902,503.

SUMMARY OF THE INVENTION

According to an aspect of the present invention, medical devices are provided whose surfaces are partially covered with a coating that further comprises silver nanoparticles.

Other aspects of the invention pertain to methods of making and using such medical devices.

An advantage of the present invention is that the coated sections of the devices prevent or inhibit microbial migration on the surface.

Another advantage of the present invention is that it requires significantly less antimicrobial material on the device, due to the fact that the device is only partially coated (albeit in strategic locations).

Yet another advantage is that coatings are provided which may be used as an indicator for placement during surgery and monitoring post surgery.

These and other aspects, embodiments and advantages of the present invention will become immediately apparent to those of ordinary skill in the art upon review of the Detailed Description and any claims to follow.

DETAILED DESCRIPTION OF THE INVENTION

Figure 1:
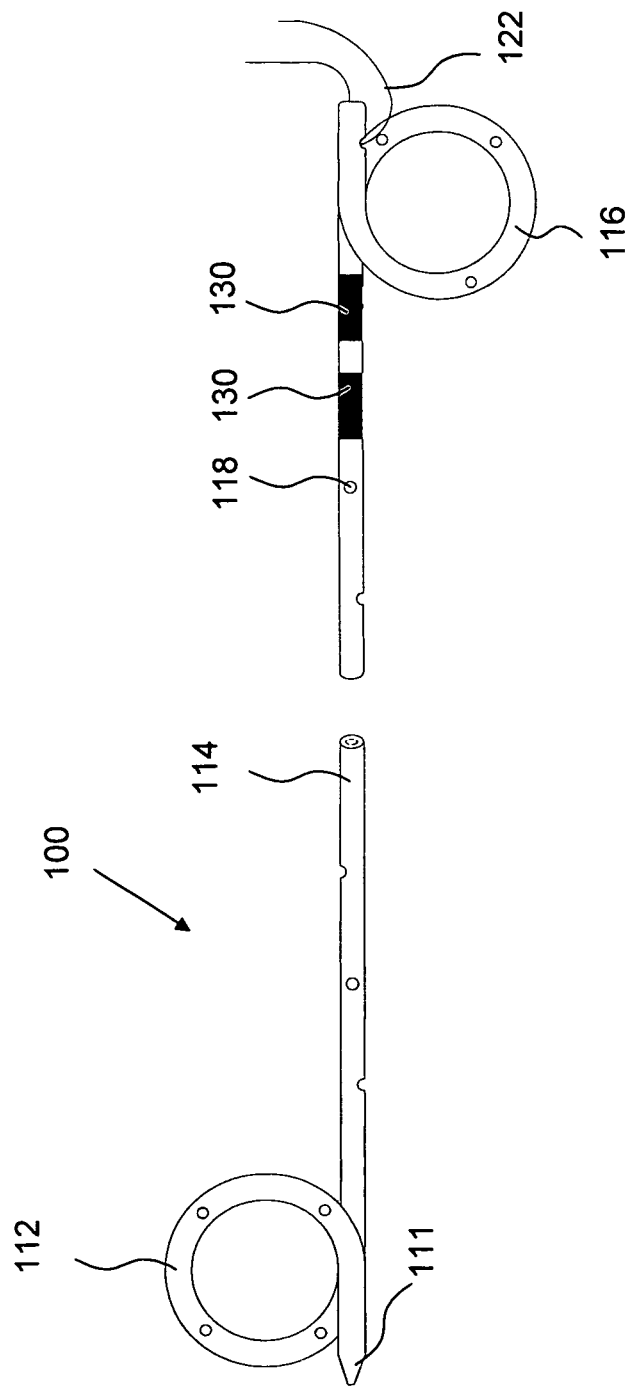
FIG. 1 is a schematic side view of a ureteral stent, in accordance with an embodiment of the invention.

A more complete understanding of the present invention is available by reference to the following detailed description of numerous aspects and embodiments of the invention. The detailed description of the invention which follows is intended to illustrate but not limit the invention.

According to an aspect of the present invention, medical devices are provided whose surfaces are partially covered with a coating that further comprises silver nanoparticles.

As used herein, "nanoparticles" have at least one dimension (e.g., the thickness) that is less than 1000 nm (e.g., at least the diameter is less than 1000 nm for a nanofiber or nanotube, at least the thickness is less than 1000 nm for a nanoplate or nanoribbon, at least the diameter is less than 1000 nm for a nanosphere, etc.). For example, nanoparticles in accordance with the invention may have at least one dimension ranging from 1000 nm to 300 nm to 100 nm to 80 nm to 60 nm to 50 nm to 40 nm to 30 nm to 20 nm to 10 nm or less. In some embodiments, nanoparticles are employed in which all dimensions (e.g., length, width, height, diameter, etc.) are less than 1000 nm.

As the name suggests, the nanoparticles used in the present invention comprise silver, typically 50 wt % or more silver (e.g. from 50 wt % to 60 wt % to 70 wt % to 80 wt % to 90 wt % to 95 wt % to 97 wt % to 99 wt % or more).

As noted above, silver is known to have good antimicrobial properties, and the same is true for silver nanoparticles. Due to their small size, silver nanoparticles have increased surface area per unit mass relative to larger particles, which leads to higher release rates than those exhibited by larger particles.

In addition to silver, the nanoparticles (and coatings) of the present invention may in some embodiments comprise additional materials besides silver, including other metals, non-metallic inorganic materials, and organic materials including small organic molecules and polymers. For instance, in some embodiments, the coatings of the present invention may further comprise a polymeric dispersion stabilizer such as polyvinyl pyrrolidone, polyacrylic acid, polyacrylamide, polymethyl methacryate or copolymers of the forgoing, among others. Dispersion stabilizers are sometimes used in forming stable liquid suspensions of nanoparticles.

Silver nanoparticle containing coatings in accordance with the invention typically contain from 25 wt % or less to 50 wt % to 60 wt % to 70 wt % to 80 wt % to 90 wt % to 95 wt % to 97 wt % to 99 wt % or more silver).

Typically, the nanoparticle containing coating is a patterned coating. For example, the nanoparticle containing coating may be in the form of one or more markers, which can assist with visual placement of the device. Moreover, as a result of the antimicrobial properties of the silver, such markers can also, for example, act to block microbial advancement along the surface of the device.

In certain embodiments of the invention, the medical devices of the invention are urological medical devices (i.e., medical devices that are suitable for placement in the urinary tract of a subject, including the kidneys (e.g., in the renal calyx, renal pelvis, etc.), ureters, bladder and urethra. These include various elongated devices including elongated devices having any of a variety of solid and hollow cross-sections including circular cross-sections (e.g., tubular and rod-shaped devices), oval cross-sections, triangular cross-sections, and rectangular cross-sections (e.g., ribbon-shaped devices), among many other regular and irregular cross-sections. Specific examples include urological stents, for example, urethral and ureteral stents, urological catheters (e.g., drainage catheters, guide catheters, etc.), guidewires, urological scopes (e.g., cytoscopes, ureteroscopes, nephroscopes, etc.), tissue engineering scaffolds, grafts and patches, among others.

In some embodiments, devices are provided which are adapted to be advanced over a guide wire or advanced through a channel, for example, one associated with a guide catheter or scope.

In some embodiments, devices may be employed that take on a particular beneficial shape in vivo, for example, immediately upon removal of a guide wire or emergence from a channel (e.g., due to elastic rebound of the material) or upon application of an external stimulus such as heat or light (e.g., where a shape memory material such as a shape memory polymer is employed). For example, the device may take on a non-linear form such as a coiled configuration. Such constructions allow the medical device to be held in place in the urinary tract, for example, by forming a coil or other retention element in the kidney (e.g., in the renal calyx and/or renal pelvis), the bladder, or both.

A schematic illustration of a ureteral stent in accordance with an embodiment of the invention is shown in FIG. 1. The stent 100 is a tubular polymeric extrusion containing a renal pigtail 112, a shaft 114 and a bladder pigtail 116. Polymeric materials for forming the tubular polymeric extrusion include polyurethane and poly(ethylene-co-vinyl acetate) (EVA). Among EVA copolymers are included random and other copolymers having a vinyl acetate weight percent ratio of from about 0.5% to 1% to 2% to 5% to 15% to 20% to 30% to 40% or more. In general, the higher the vinyl acetate content, the lower the stiffness and Durometer of the EVA. A tubular polymeric extrusion may be produced having distinct end regions of different Durometer value with a transitional region in between.

The stent 100 shown is further provided with the following: (a) a tapered tip 111, to aid insertion, (b) multiple side ports 118 (one numbered), which are arranged in a spiral pattern down the length of the body to promote drainage, and (c) a Nylon suture 122, which aids in positioning and withdrawal of the stent, as is known in that art. During placement, such ureteral stents 100 are typically placed over a urology guide wire, through a cystoscope and advanced into position with a positioner. Once the proximal end of the stent is advanced into the kidney/renal calyx, the guide wire is removed, allowing pigtails 112, 116 to form in the kidney and bladder.

In accordance with the present invention, the stent 100 also contains one or more graduation marks 130 in the form of a silver-nanoparticle-containing coating (two bands are illustrated near the bladder retention element 116 of the stent), which may be used for visualization by the physician to know when the appropriate length of stent has been inserted into the ureter. Moreover, because the marks 130 contain silver nanoparticle in accordance with the invention, the marks 130 also act as barriers to microbial advancement from the bladder-to-kidney direction. In other words, because one or more bands of silver-nanoparticle-containing coating are applied to the bladder end of the device (i.e., the infection end), microbial migration along the device in the direction of the kidney end of the device is prevented or substantially diminished.

The present invention also pertains to medical devices other than urological medical devices, including, for example, vascular catheters, dialysis catheters, wound dressings, and surgical grafts, including surgically implantable meshes, particularly meshes for pelvic floor repair, urethral slings, hernia meshes (e.g., meshes for inguinal hernia, hiatus hernia, etc.), meshes for thoracic wall defects, breast support meshes and various other soft-tissue surgical mesh support devices, including meshes for cosmetic and reconstructive surgery, among others.

Surgical meshes in accordance with the present invention may be in the form of ribbons, sheets, and other more complex sheet-like shapes. Surgical meshes in accordance with the present invention are typically formed using one or more filaments (e.g., fibers, fibrils, threads, yarns, etc.). Thus, surgical meshes in accordance with the present invention include monofilament and multifilament meshes. Surgical meshes in accordance with the present invention include woven meshes and non-woven meshes (including knitted meshes, felt meshes, and spunbound meshes, among others). Surgical meshes in accordance with the present invention include meshes having small pores (less than 1 mm) and those having large pores (greater than or equal to 1 mm). Typically, the pores within the surgical meshes are greater than 5 microns in diameter.

Filaments for forming meshes in accordance with the present invention include polymeric filaments which remain intact in vivo (i.e., non-bioresorbable polymeric filaments) such as those formed from (a) polyolefins, including homopolymers and copolymers of C1-C8 alkenes, for example, polypropylene, (b) fluoropolymers, including homopolymers and copolymers of C1-C8 alkenes in which one or more hydrogen atoms are substituted with fluorine, for example, polytetrafluoroethylene and polyvinylidene fluoride, and (c) polyesters, including, for example, polyethylene terephthalate, among various other polymers.

A popular treatment of stress urinary incontinence (SUI) is via the use of a surgical mesh, commonly referred to as a sling, which is permanently placed under a patient's bladder neck or mid-urethra to provide a urethral platform. Placement of the sling limits the endopelvic fascia drop, while providing compression to the urethral sphincter to improve coaptation. Further information regarding sling procedures may be found, for example, in the following: Fred E. Govier et al., "Pubocaginal slings: a review of the technical variables," *Curr. Opin Urol.* 11:405-410, 2001, John Klutke and Carl Klutke, "The promise of tension-free vaginal tape for female SUI," *Contemporary Urol.* pp. 59-73, October 2000; and PCT Patent Publication No. WO 00/74633 A2: "Method and Apparatus for Adjusting Flexible Areal Polymer Implants."

Figure 4:
FIG. 4 is a schematic top view of a surgical mesh, in accordance with yet another embodiment of the invention.

There is schematically illustrated in FIG. 4, a mesh 400, such as a urethral sling, which includes a mesh material 410 and two regions 430 wherein the mesh is coated with a coating that further comprises silver nanoparticles, in accordance with the invention. As above, the coated regions 430 may act as markers for visualization by the physician and also act as barriers to microbial advancement along the length of the mesh 400.

Pelvic floor (pelvic support) disorders involve a dropping down (prolapse) of the bladder, rectum, or uterus caused by weakness of or injury to the ligaments, connective tissue, and muscles of the pelvis. As with SUI, treatment of pelvic floor disorders are commonly treated by permanently implanting a surgical mesh within the patient's pelvis to support the organ or organs that require support.

Figure 2:
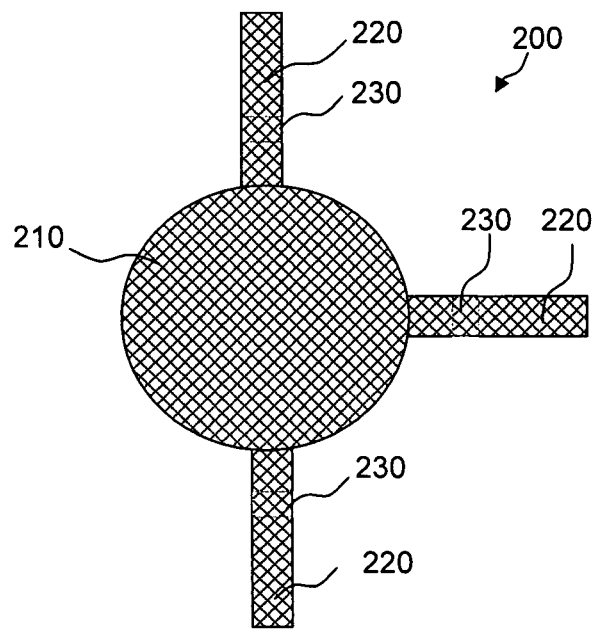
FIG. 2 is a schematic top view of a surgical mesh, in accordance with an embodiment of the invention.

In accordance with another embodiment of the invention, there is schematically illustrated in FIG. 2, a mesh 200, for example, a pelvic floor repair mesh, having a central portion 210 and a plurality of arms 220 that emanate from the central portion 210. Each arm 220 is provided with a region 230 wherein the mesh is coated with a coating that further comprises silver nanoparticles, in accordance with the invention. As above, the coated regions 230 may act as markers for visualization by the physician and also act as barriers to microbial advancement along the length of the arms 220.

Figure 3:
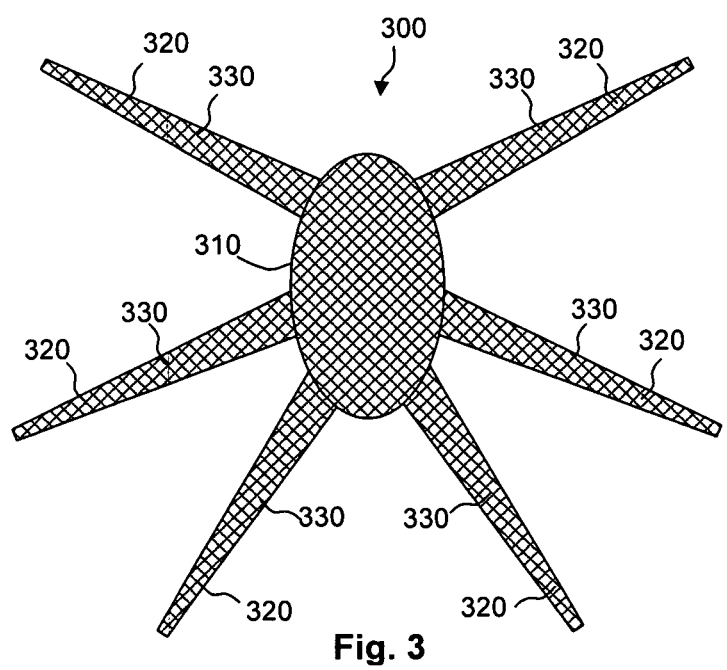
FIG. 3 is a schematic top view of a surgical mesh, in accordance with another embodiment of the invention.

Although the mesh of FIG. 2 has three rectangular arms and a circular body portion, other shapes and numbers of arms may be used (e.g., 1, 2, 4, 5, 6, 7, 8, etc.). As one specific variation, FIG. 3 illustrates a mesh 300 having a non-circular (oval) central body portion 310 and six non-rectangular (trapezoidal) arms 320, among near limitless other possibilities. As above, each arm 320 is provided with a region 330 wherein the mesh is coated with a coating that further comprises silver nanoparticles, which coated regions 330 may act as markers for visualization by the physician and also act as barriers to microbial advancement along the length of the arms 320.

Medical devices which may be coated with the coatings of the invention are not limited to any particular material and can be formed, for example, from polymeric materials, ceramic materials, metallic materials, and combinations of the same. In certain embodiments, polymers are preferred.

Polymers for forming medical devices in accordance with the invention may be selected from suitable members of the following, among others: polycarboxylic acid polymers and copolymers including polyacrylic acids; acetal polymers and copolymers; acrylate and methacrylate polymers and copolymers (e.g., n-butyl methacrylate); cellulosic polymers and copolymers; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; polycarbonates; polyacrylonitriles; polyvinylpyrrolidones; polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropenes) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers; as well as blends and further copolymers of the above.

The urological medical devices of the invention may also contain (e.g., on or within a material forming the medical device, on or within the silver nanoparticle containing coatings, etc.) effective amounts of one or more optional supplemental agents.

Such optional supplemental agents may include, for example, supplemental therapeutic agents such as corticosteroids, narcotic and non-narcotic analgesics, local anesthetic agents, antibiotics and combinations thereof, among others.

Other examples of optional supplemental agents include imaging agents, for instance, (a) contrast agents for use in connection with x-ray fluoroscopy, including metals, metal salts and oxides (particularly bismuth salts and oxides), and iodinated compounds, among others, (b) contrast agents for use in conjunction with ultrasound imaging, including inorganic and organic echogenic particles (i.e., particles that result in an increase in the reflected ultrasonic energy) or inorganic and organic echolucent particles (i.e., particles that result in a decrease in the reflected ultrasonic energy), and (c) contrast agents for use in conjunction with magnetic resonance imaging (MRI), including contrast agents that contain elements with relatively large magnetic moment such as Gd(III), Mn(II), Fe(III) and compounds (including chelates) containing the same, such as gadolinium ion chelated with diethylenetriaminepentaacetic acid.

Other aspects of the invention pertain to methods by which medical devices may be provided with silver nanoparticle containing coatings.

In some aspects, the silver nanoparticle containing coatings are applied in the form of a liquid formulation using a suitable application device, for example, a sprayer, brush, roller, printer (e.g., screen printing device, ink jet printer, etc.)

Liquid formulations in some embodiments comprise nanoparticles dispersed in a solvent system comprising one or more solvent species. For example, relatively hydrophilic liquid formulations may be formulated using polar solvent species such as one or more of water, methanol, ethanol, ethylene glycol and glycerol, among many others. Relatively hydrophobic liquid formulations may be formulated using non-polar solvent species such as one or more of toluene, and tetradecane, among many others. In general hydrophilic liquid formulations will better coat hydrophilic medical device surfaces, whereas hydrophobic liquid formulations will better coat hydrophobic medical device surfaces.

Liquid formations may also contain one or more polymeric dispersion stabilizers, for example, selected from polyvinyl pyrrolidone, polyacrylic acid, polyacrylamide, polymethyl methacryate and copolymers of the forgoing, among many others.

Various printable liquid formulations that contain silver nanoparticles, which may be used to form the coatings in accordance with the invention, are described, for example, in Pub. Nos. US 2004/0147618 to Lee et al., US 2007/0034052 and US 2006/0189113 to Vanheusden et al., US 2006/0254387 and 2007/0018140 to Lee et al., and US 2005/0078158 to Magdassi et al.

Specific examples of commercially available printable nanoparticle dispersions are NDSilver nanoparticle dispersions, which include dispersions of 30-40 nm spherical silver particles or 80 nm spherical silver particles, in ethanol or in water (Nano Dynamics, Inc., Buffalo, N.Y., USA).

In other embodiments, that/those portion/portions of the medical device for which a silver-nanoparticle-containing coating is desired is dipped into a solution from which silver nanoparticles become seeded on the immersed portion/portions of the device. Such technology is described, for example, in Pub. No. US 20070003603 to Karandikar et al. and in U.S. Pat. Nos. 5,928,174, 6,355,858, 6,605,751 or 6,897,349 to AcryMed, Inc. In still other embodiments, the medical devices are provided with a polymeric coating upon which such silver nanoparticles are seeded. For example, the coating may be a hydrophilic coating such as Hydroplus® crosslinked polyacrylic acid coatings available from Boston Scientific, Natick, Mass., USA.

Various aspects of the invention of the invention relating to the above are enumerated in the following paragraphs:

Aspect 1. A medical device comprising a medical device substrate that is partially covered with a coating that comprises silver nanoparticles.

Aspect 2. The medical device of aspect 1, wherein the coating is in the form of a marker that assists with visual placement or position confirmation of the device.

Aspect 3. The medical device of aspect 1, wherein the device is an elongated device of solid or hollow cross-section.

Aspect 4. The medical device of aspect 3, wherein the coating comprises a band that extends around the circumference of the elongated device.

Aspect 5. The medical device of aspect 4, wherein the medical device is a tubular medical device.

Aspect 6. The medical device of aspect 5, wherein the tubular medical device is a ureteral stent.

Aspect 7. The medical device of aspect 1, wherein the medical device comprises an elongated mesh.

Aspect 8. The medical device of aspect 7, wherein the medical device is a surgical mesh that comprises an arm.

Aspect 9. The medical device of aspect 8, wherein the coating is provided across the entire width of the arm.

Aspect 10. The medical device of aspect 9, wherein the medical device comprises a plurality of arms.

Aspect 11. The medical device of aspect 1, wherein the coating comprises nanoparticles in which all dimensions are less than 100 nm.

Aspect 12. The medical device of aspect 1, wherein the nanoparticles comprise at least 75 wt % silver.

Aspect 13. The medical device of aspect 1, wherein the nanoparticles comprise at least 95 wt % silver.

Aspect 14. The medical device of aspect 1, wherein the coating comprises at least 50 wt % silver.

Aspect 15. The medical device of aspect 1, wherein the coating comprises at least 75 wt % silver.

Aspect 16. The medical device of aspect 1, wherein the medical device further comprises an agent selected from a corticosteroid, a narcotic analgesic, a non-narcotic analgesic, a local anesthetic agent, an antibiotic, an imaging contrast agent, and a combination of the forgoing.

Aspect 17. The medical device of aspect 1, wherein the medical device substrate comprises a hydrophilic polymeric coating.

Aspect 18. A method of forming the medical device of aspect 1, comprising applying a liquid formulation that comprises the nanoparticles to the medical device substrate.

Aspect 19. The method of aspect 18, wherein the liquid formulation further comprises one or more solvent species.

Aspect 20. The method of aspect 18, wherein the liquid formulation further comprises a dispersion stabilizer.

Aspect 21. The method of aspect 18, wherein the liquid formulation is applied using a printing technique.

Aspect 22. A method of forming the medical device of aspect 1, comprising immersing the medical device substrate into a solution whereby the silver nanoparticles precipitate onto the device substrate.

Aspect 23. The method of aspect 22, wherein the medical device substrate comprises a hydrophilic polymeric coating and wherein the silver nanoparticles are precipitated onto the coating.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. A medical device comprising a medical device substrate that is partially covered with a coating that comprises silver nanoparticles, which confer antimicrobial properties to the device upon implantation of the device, wherein said device is a ureteral stent, and wherein said coating is in the form of a marker which assists with visual placement or position confirmation of said device and which acts as a barrier to microbial advancement from the bladder-to-kidney direction upon implantation of the device.

2. The medical device of claim 1, wherein said marker comprises a band that extends around the circumference of said ureteral stent.

3. The medical device of claim 1, wherein said coating comprises nanoparticles in which all dimensions are less than 100 nm.

4. The medical device of claim 1, wherein said nanoparticles comprise at least 75 wt % silver.

5. The medical device of claim 1, wherein said nanoparticles comprise at least 95 wt % silver.

6. The medical device of claim 1, wherein said coating comprises at least 50 wt % silver.

7. The medical device of claim 1, wherein said coating comprises at least 75 wt % silver.

8. The medical device of claim 1, wherein said medical device further comprises an agent selected from a corticosteroid, a narcotic analgesic, a non-narcotic analgesic, a local anesthetic agent, an antibiotic, an imaging contrast agent, and a combination of the forgoing.

9. The medical device of claim 1, wherein said medical device substrate comprises a hydrophilic polymeric coating.

10. The medical device of claim 1, comprising a plurality of said markers.

11. The medical device of claim 10, wherein said markers are in the form of bands that extend around the circumference of said device.

12. The medical device of claim 11, wherein said ureteral stent comprises a substantially linear central portion, a kidney coil retention element, a bladder coil retention element, and a substantially linear portion between the kidney coil retention element and the bladder coil retention element.

13. The medical device of claim 12, wherein said marker bands are disposed on the substantially linear portion of the stent near the bladder coil retention element.

14. The medical device of claim 11, wherein said coating comprises at least 50 wt % silver.

15. The medical device of claim 11, wherein said coating comprises at least 75 wt % silver.

* * * * *